US008450454B2

(12) United States Patent
Yan et al.

(10) Patent No.: US 8,450,454 B2
(45) Date of Patent: May 28, 2013

(54) COMPOSITIONS FOR INHIBITING ABAD/ABETA PROTEIN INTERACTION

(75) Inventors: Shi Du Yan, Tenafly, NJ (US); David M. Stern, Cincinnati, OH (US); Joyce W. Lustbader, Tenafly, NJ (US); Hao Wu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/006,309

(22) Filed: Jan. 13, 2011

(65) Prior Publication Data

US 2011/0171194 A1 Jul. 14, 2011

Related U.S. Application Data

(63) Continuation of application No. 11/578,401, filed as application No. PCT/US2005/012482 on Apr. 12, 2005, now abandoned.

(60) Provisional application No. 60/561,859, filed on Apr. 12, 2004.

(51) Int. Cl.
*C07K 2/00* (2006.01)
*C07K 4/00* (2006.01)
*C07K 5/00* (2006.01)
*C07K 7/00* (2006.01)
*C07K 14/00* (2006.01)

(52) U.S. Cl.
USPC .............. 530/300; 530/350; 530/324; 436/89

(58) Field of Classification Search
None
See application file for complete search history.

(56) References Cited

U.S. PATENT DOCUMENTS 6,268,479 B1    7/2001   Stern et al.
2002/0132319 A1  9/2002   Abreo et al.

FOREIGN PATENT DOCUMENTS

WO    WO 98/40484 A1       9/1998
WO        CA2442705    *  12/2002
WO    WO 03/087768 A2     10/2003

OTHER PUBLICATIONS

Morris et al. Nat Biotechnol. 2001, 19: 1173-1176.*
K. Beyreuther, C.L. Masters, Nature 389, 677-8 (1997).
S.D. Yan, et al., J. Biol Chem 274, 2145-56 (1999).
L. Torroja, D. Ortuno-Sahagun, A. Ferrus, B. Hammerle, J.A. Barbas, J Cell Biol 141, 1009-17 (1998).
L. Mucke, et al., J. Neurosci 20, 4050-8 (Jun. 1, 2000).
S.D. Yan et al., J. Biol. Chem 275, 27100-9 (2000).
A.J. Powell, et al., J Mol Biol 303, 311-27 (2000).
M. Aarts, et al., Science 298, 846-50 (Oct. 25, 2002).
M. Becker-Hapak, S.S. McAllister, S.F. Dowdy, Methods 24, 247-56 (Jul. 2001).
H.P. Grill, J.L. Zweier, P. Kuppusamy, M.L. Weisfeldt, J.T. Flaherty, J Am Coll Cardiol 20, 1604-11 (Dec. 1992).
D. Morgan, et al,, Nature 408, 982-5 (Dec. 21-28, 2000).
G. Di Rosa, T. Odrijin, R.A. Nixon, O. Arancio, J Mol Neurosci 19, 135-41 (Aug.-Oct. 2002).
R.H. Swerdlow, S.J. Kish, Int Rev Neurobuil 53, 341-85 (2002).
R. Castellani, et al., J Neurosci Res 70, 357-60 (Nov. 1, 2002).
A.D. Cash, et al., Neuroscientist 8, 489-96 (Oct. 2002).
J.P. Blass, Int Rev Neurobiol 51, 325-76 (2002).
A.C. Rego, C.R. Oliveira, Neurochem Res 28, 1563-74 (Oct. 2003).
G. Aliev, et al., Neural Res 25, 665-74 (Sep. 2003).
J.P. Blass, Neurol Res 25, 556-66 (Sep. 2003).
M.P. Mattson, Int Rev Neurobiol 53, 387-409 (2002).
H.K. Anandatheerthavarada, G., Biswas, M.A. Robin, N.G. Avadhani, J Cell Biol 161, 41-54 (Apr. 14, 2003).
Z. Otwinowski, W. Minor, Methods Enzymol. 276, 307-326 (1997).
L. Tong, J. Appl. Cryst. 26, 748-751 (1993).
A.T. Brunger et al., Acta Crystallogr. D54, 905-21 (1998).
T.A. Jones, J.-Y. Zou, S.W. Cowan, M. Kjeldgaard, Acta Crystallgr. A47, 110-119 (1991).
S.V. Evans, J. Mol. Graph. 11, 134-8 (1993).
T. Valdes-Gonzalez, J. Inagawa, T. Ido, Peptides 22, 1099-106 (Jul. 2001).
K. Takuma, et al., J Biol Chem 276, 48093-9 (Dec. 21, 2001).
J.P. Crow, Nitric Oxide: Biology and Chemistry 1, 145-157 (1997).
N.W. Kooy, J.A. Royall, H. Ischiropoulos, Free Radic Res 27, 245-54 (Sep. 1997).
L.F. Lue et al., Experimental Neurology 171, 29-45 (2001).
Yan et al. (1997) "An Intracellular Protein That Binds Amyloid-β Peptides And Mediates Neurotoxicity In Alzheimer's Disease" Nature 06, Oct. 1997, vol. 389, pp. 689-695.
Christen, Y. "Oxidative Stress And Alzheimer's Disease" Am J Clin Nutr 2000, vol. 71 (suppl): 621S-9S.
Yan et al. "Cellular Cofactors For Amyloid-β Peptide-Induced Cell Stress" Am J Pathol, Nov. 1989, vol. 155, No. 5, pp. 1403-1411.
Opperman et al. "Binding Of Amyloid-β Peptide To Mitochondrial Hydroxyacyl-CoA Dehydrogenase (ERAB): Regulation Of An SDR Enzyme Activity With Implications For Apoptosis In Alzheimer's Disease" FEBS Letters, 1999, vol. 451, pp. 238-242.
Amendment In Response To Nov. 13, 2009 Final Office Action filed Dec. 14, 2009 in connection with U.S. Appl. No. 11/578,401, filed Jan. 25, 2008.
Amendment In Response To Feb. 17, 2010 Office Action filed Jul. 19, 2010 in connection with U.S. Appl. No. 11/578,401, filed Jan. 25, 2008.

(Continued)

*Primary Examiner* — Chang-Yu Wang
(74) *Attorney, Agent, or Firm* — John P. White; Cooper & Dunham LLP

(57) ABSTRACT

This invention provides methods, compositions and articles of manufacture for inhibiting binding between Aβ protein and ABAD in cells. Uses of this invention include, for example, treating Alzheimer's disease; reducing free radical generation, DNA fragmentation, and cytochrome C release in cells; and preserving cell viability by preventing LDH release from a cell.

4 Claims, 8 Drawing Sheets

OTHER PUBLICATIONS

Amendment In Response To Oct. 13, 2010 Final Office Action filed Dec. 29, 2010 in connection with U.S. Appl. No. 11/578,401, filed Jan. 25, 2008.

Office Action issued Nov. 13, 2009 in connection with U.S. Appl. No. 11/578,401, filed Jan. 25, 2008.

Office Action issued Feb. 17, 2010 in connection with U.S. Appl. No. 11/578,401, filed Jan. 25, 2008.

Final Office Action issued Oct. 13, 2010 in connection with U.S. Appl. No. 11/578,401, filed Jan. 25, 2008.

* cited by examiner

US 8,450,454 B2

COMPOSITIONS FOR INHIBITING ABAD/ABETA PROTEIN INTERACTION

This application is a continuation of U.S. Ser. No. 11/578,401, filed Jan. 25, 2008, now abandoned, a §371 national stage of PCT/US2005/012482 filed Apr. 12, 2005, and claims the benefit of U.S. Provisional Application No. 60/561,859, filed Apr. 12, 2004, the entire contents of each of which are hereby incorporated by reference into this application.

This invention was made with government support under grant numbers NS36630, AG18440, AG02207, and UL1 RR0241456 awarded by the National Institutes of Health (NIH). The government has certain rights in the invention.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

Human Aβ-binding alcohol dehydrogenase ("ABAD," also known as "ERAS" and "HSD-10") was the only protein identified from four positive clones that bound Aβ protein (also referred to as "Aβ") in a yeast two-hybrid screen against human brain and HeLa cDNA libraries (1, 2). Biochemical characterization has established that the interaction between ABAD and Aβ is highly specific and starts to occur at nanomolar concentrations. At micromolar concentrations, Aβ, likely in its oligomeric form, inhibits ABAD enzymatic activity (1, 3, 4). ABAD appears to have an essential physiological role in mitochondria (1, 3), and mutational inactivation of *Drosophilia* ABAD (scully) resulted in a lethal phenotype (5). ABAD is up-regulated in affected neurons in AD (1) (FIG. 5) and co-expression of ABAD with mutant amyloid precursor protein (mAPP) exacerbates Aβ-induced cellular oxidant stress and cell death (1, 3).

SUMMARY OF THE INVENTION

This invention provides a polypeptide consisting of a portion of ABAD, wherein the portion of ABAD binds to Aβ protein and comprises the sequence of amino acid residues 94-114 of ABAD.

This invention further provides a composition of matter comprising (a) a pharmaceutical carrier, and (b) a polypeptide consisting of a portion of ABAD, wherein the portion of ABAD binds to Aβ protein and comprises the sequence of amino acid residues 94-114 of ABAD.

This invention further provides a composition of matter comprising a polypeptide consisting of a portion of ABAD comprising the sequence of amino acid residues 94-114 of ABAD, wherein the composition binds to Aβ protein.

This invention further provides a composition of matter comprising (a) a Tat protein operatively affixed to (b) a polypeptide consisting of a portion of ABAD comprising the sequence of amino acid residues 94-114 of ABAD, wherein the composition binds to Aβ protein.

This invention further provides a polypeptide consisting of a portion of Aβ protein, wherein the portion of Aβ protein binds to ABAD and comprises the sequence of amino acid residues 1-20 of Aβ protein.

This invention further provides a composition of matter comprising (a) a pharmaceutical carrier, and (b) a polypeptide consisting of a portion of Aβ protein, wherein the portion of Aβ protein binds to ABAD and comprises the sequence of amino acid residues 1-20 of Aβ protein.

This invention further provides a composition of matter comprising a polypeptide consisting of a portion of Aβ protein comprising the sequence of amino acid residues 1-20 of Aβ protein, wherein the composition binds to ABAD.

This invention further provides a composition of matter comprising (a) a Tat protein operatively affixed to (b) a polypeptide consisting of a portion of Aβ protein comprising the sequence of amino acid residues 1-20 of Aβ protein, wherein the composition binds to ABAD.

This invention further provides a method for treating a subject afflicted with Alzheimer's disease comprising administering to the subject a therapeutically effective amount of an agent that inhibits binding between Aβ protein and ABAD in the subject's cells.

This invention further provides a method for reducing free radical generation in a cell comprising introducing into the cell an agent that inhibits binding between Aβ protein and ABAD.

This invention further provides a method for reducing DNA fragmentation in the cytosol of a cell comprising delivering into the cell an agent that inhibits binding between Aβ protein and ABAD.

This invention further provides a method for reducing cytochrome c release from mitochondria in a cell comprising introducing into the cell an agent that inhibits binding between Aβ protein and ABAD.

This invention further provides a method for preserving cell viability by reducing LDH release from a cell comprising introducing into the cell an agent that inhibits binding between Aβ protein and ABAD.

This invention further provides an article of manufacture comprising a packaging material having therein a polypeptide consisting of a portion of ABAD, wherein the portion of ABAD binds to Aβ protein and comprises the sequence of amino acid residues 94-114 of ABAD, and wherein the packaging material has affixed thereto a label indicating a use for the polypeptide for treating a subject afflicted with Alzheimer's disease.

This invention further provides an article of manufacture comprising a packaging material having therein a composition of matter comprising a polypeptide consisting of a portion of ABAD comprising the sequence of amino acid residues 94-114 of ABAD, wherein the composition binds to Aβ protein, and wherein the packaging material has affixed thereto a label indicating a use for the composition for treating a subject afflicted with Alzheimer's disease.

This invention further provides an article of manufacture comprising a packaging material having therein a polypeptide consisting of a portion of Aβ protein, wherein the portion of Aβ protein binds to ABAD and comprises the sequence of amino acid residues 1-20 of Aβ protein, and wherein the packaging material has affixed thereto a label indicating a use for the polypeptide for treating a subject afflicted with Alzheimer's disease.

This invention further provides an article of manufacture comprising a packaging material having therein a composition of matter comprising a polypeptide consisting of a portion of Aβ protein comprising the sequence of amino acid residues 1-20 of Aβ protein, wherein the composition binds to ABAD, and wherein the packaging material has affixed thereto a label indicating a use for the composition for treating a subject afflicted with Alzheimer's disease.

This invention further provides a method for determining whether an agent inhibits the binding of Aβ protein to ABAD, which comprises: (a) admixing (i) a polypeptide consisting of a portion of ABAD, wherein the portion of ABAD binds to Aβ protein and comprises the sequence of amino acid residues 94-114 of ABAD, (ii) Aβ protein, and (iii) the agent, under conditions which would permit binding of the polypeptide and Aβ protein in the absence of the agent; (b) determining the amount of polypeptide bound to Aβ protein in step (a); and (c) comparing the amount of bound polypeptide determined in step (b) with the amount determined in the absence of the agent, whereby a lower amount of binding in the presence of the agent indicates that the agent inhibits the binding of Aβ protein to ABAD.

This invention further provides a method for determining whether an agent inhibits the binding of Aβ protein to ABAD, which comprises: (a) admixing (i) a polypeptide consisting of a portion of Aβ protein, wherein the portion of Aβ protein binds to ABAD and comprises the sequence of amino acid residues 1-20 of Aβ protein, (ii) ABAD, and (iii) the agent, under conditions which would permit binding of the polypeptide and ABAD in the absence of the agent; (b) determining the amount of polypeptide bound to ABAD in step (a); and (c) comparing the amount of bound polypeptide determined in step (b) with the amount determined in the absence of the agent, whereby a lower amount of binding in the presence of the agent indicates that the agent inhibits the binding of Aβ protein to ABAD.

Finally, this invention provides a method for determining whether an agent inhibits the binding of Aβ protein to ABAD, which comprises: (a) admixing (i) a polypeptide consisting of a portion of ABAD, wherein the portion of ABAD binds to Aβ protein and comprises the sequence of amino acid residues 94-114 of ABAD, (ii) a polypeptide consisting of a portion of Aβ protein, wherein the portion of Aβ protein binds to ABAD and comprises the sequence of amino acid residues 1-20 of Aβ protein, and (iii) the agent, under conditions which would permit binding of the portion of ABAD and the portion of A protein in the absence of the agent; (b) determining the amount of portion of ABAD bound to portion of A protein in step (a); and (c) comparing the amount of the bound portion of ABAD determined in step (b) with the amount determined in the absence of the agent, whereby a lower amount of binding in the presence of the agent indicates that the agent inhibits the binding of Aβ protein to ABAD.

DETAILED DESCRIPTION OF THE INVENTION

Definitions

Figure 1:
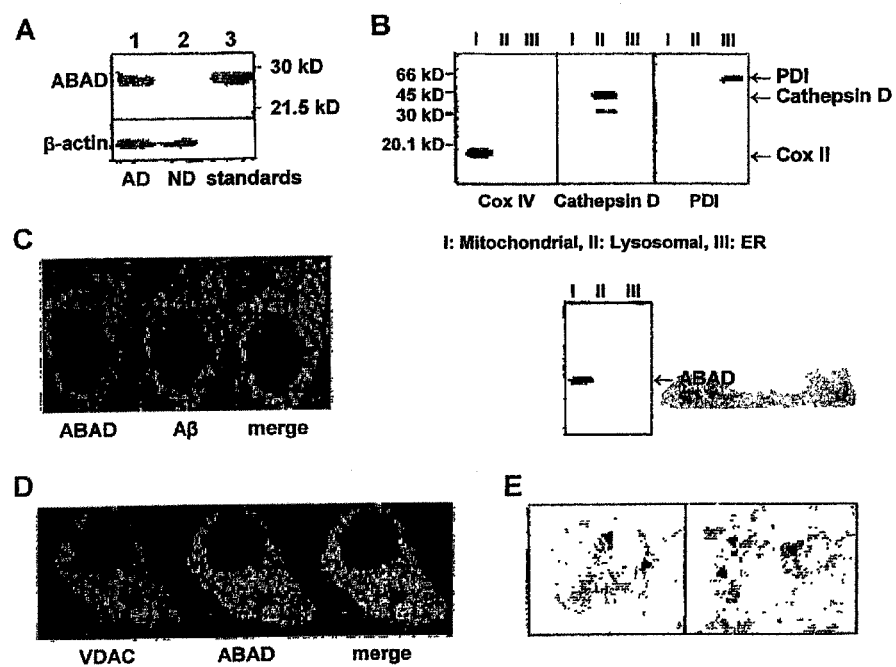
FIG. 1. ABAD-Aβ association in AD patients and transgenic mice. (A) Co-immunoprecipitation of ABAD and Aβ in AD patient brains. Results shown are representative of the 3 patients in each group. (B) Subcellular fractionation was used to prepare fractions of mouse brain enriched for mitochondrial (fraction I), lysosomal (fraction II) or endoplasmic reticulum (fraction III) constituents. Each fraction (20 μg total protein per lane) was immunoblotted with antibodies to Cox IV (cytochrome c oxidase IV), Cathepsin D and protein disulfide isomerase (PDI). Protein loading was identical in each case. Lower panel shows the presence of ABAD in the mitochondrial fraction. (C) Co-localization of ABAD and Aβ in cerebral cortex of AD patients (magnification 200-fold). (D) Mitochondrial localization of ABAD in cerebral cortex of AD patients (magnification 200-fold). VDAC (Voltage-Dependent Anion Channel) was used as a mitochondrial marker. Mouse anti-VDAC (20 μg/ml), guinea pig anti-ABAD (10 μg/ml) and rabbit anti-Aβ (5 μg/ml) IgGs were used in C-D. (E) Colocalization of ABAD and Aβ in mitochondria of the brain of a patient with AD using electron microscopy. Double immunogold staining was performed with rabbit anti-Aβ IgG and mouse anti-ABAD IgG followed by goat anti-rabbit IgG conjugated to 12 nm gold particles (for Aβ1-42) and goat anti-mouse IgG conjugated to 18 nM gold particles (for ABAD). Arrowheads depict gold particles localizing ABAD antigen. The smaller gold particles represent sites of localization of Aβ.

"Administering" shall mean delivering in a manner which is effected or performed using any of the various methods and delivery systems known to those skilled in the art. Administering can be performed, for example, intravenously, pericardially, orally, via implant, trans-mucosally, transdermally, intramuscularly, subcutaneously, intraperitoneally, intrathecally, intra-lymphatically, intralesionally, or epidurally. Administering can be performed, for example, once, a plurality of times, and/or over one or more extended periods.

"Agent" shall include, without limitation, an organic compound, a nucleic acid, a polypeptide, a lipid, and a carbohydrate. Agents include, for example, agents which are known with respect to structure and/or function, and those which are not known with respect to structure or function.

"Inhibit," when used in connection with the binding between Aβ and ABAD, shall mean to reduce such binding. In one embodiment, "inhibit" shall mean to eliminate such binding. In the preferred embodiment, inhibiting binding between two proteins means to specifically inhibit such binding, i.e., to reduce or eliminate binding between those two proteins without reducing or eliminating binding between other proteins at all or to as great a degree.

"Operatively affixed," with respect to a first protein joined to a second protein, means affixed in a manner permitting each protein to perform at least one function which it would perform were it not affixed to the other protein.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer=s dextrose, and the like. Preservatives and other additives may also be present, such as, for example, antimicrobials, antioxidants, chelating agents, inert gases, and the like.

The terms "polypeptide," "peptide" and "protein" are used interchangeably herein, and each means a polymer of amino acid residues.

"Subject" shall mean any animal, such as a human, non-human primate, mouse, rat, guinea pig or rabbit.

"Tat", "HIV Tat protein" and "Tat protein" are equivalent, and each shall mean any of (a) the HIV protein having the amino acid sequence met-glu-pro-val-asp-pro-arg-leu-glu-pro-trp-lys-his-pro-gly-ser-gln-pro-lys-thr-ala-cys-thr-asn-cys-tyr-cys-lys-lys-cys-cys-phe-his-cys-gln-val-cys-phe-ile-thr-lys-ala-leu-gly-ile-ser-tyr-gly-arg-lys-lys-arg-arg-gln-arg-arg-arg-pro-pro-gln-gly-ser-gln-thr-his-gln-val-ser-leu-ser-lys-gln-pro-thr-ser-gln-ser-arg-gly-asp-pro-thr-qly-pro-lys-glu (SEQ ID NO. 1), (b) the HIV protein having the amino acid sequence tyr-gly-arg-lys-lys-arg-arg-gln-arg-arg-arg (SEQ ID NO. 2), and (c) all naturally occurring variants of proteins (a) and (b). Naturally occurring variants of HIV protein sequences can be found, inter alia, in Genbank and the Los Alamos HIV Database, both well know in the art.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

EMBODIMENTS OF THE INVENTION

This invention provides methods, compositions and articles of manufacture for inhibiting neurotoxicity in Alzheimer's disease. This invention is based on the surprising discovery that Aβ protein binds to ABAD in the mitochondria.

Specifically, this invention provides a polypeptide consisting of a portion of ABAD, wherein the portion of ABAD binds to Aβ protein and comprises the sequence of amino acid residues 94-114 of ABAD. In the preferred embodiment of this polypeptide, the ABAD is human ABAD. In the preferred embodiment, this and other polypeptides of the instant invention are isolated (e.g. free from other proteins), or enriched (e.g. having only minimal (<50% total weight) protein impurities). The full sequence of human ABAD is set forth in (1) at page 690, Figure D. The sequence of amino acid residues 92-120 of human ABAD is as follows: AGIAVASKTYN-LKKGQTHTLEDFQRVLDV (SEQ ID NO. 3). The sequence of amino acid residues 94-114 of human ABAD is as follows: IAVASKTYNLKKGQTHTLEDF (SEQ ID NO. 4).

This invention further provides a composition of matter comprising (a) a pharmaceutical carrier, and (b) a polypeptide consisting of a portion of ABAD, wherein the portion of ABAD binds to Aβ protein and comprises the sequence of amino acid residues 94-114 of ABAD.

This invention further provides a composition of matter comprising a polypeptide consisting of a portion of ABAD comprising the sequence of amino acid residues 94-114 of ABAD, wherein the composition binds to Aβ protein. In the preferred embodiment of this composition, the ABAD is human ABAD. In another embodiment, the composition is further comprised by a pharmaceutical carrier.

This invention further provides a composition of matter comprising (a) a Tat protein operatively affixed to (b) a polypeptide consisting of a portion of ABAD comprising the sequence of amino acid residues 94-114 of ABAD, wherein the composition binds to Aβ protein. In the preferred embodiment of this composition, the ABAD is human ABAD. In another embodiment, the composition is further comprised by a pharmaceutical carrier.

This invention further provides for an isolated polypeptide consisting of a portion of Aβ protein, wherein the portion of Aβ protein binds to ABAD and comprises the sequence of amino acid residues 1-20 of Aβ protein. In the preferred embodiment of this polypeptide, the Aβ protein is human Aβ protein. The full, sequence of human Aβ is set forth in (1) at page 690, FIG. 1. The sequence of amino acid residues 1-20 of human Aβ is as follows: DAEFRHDSGYEVHHQKLVFF (SEQ ID NO. 5).

This invention further provides a composition of matter comprising (a) a pharmaceutical carrier, and (b) a polypeptide consisting of a portion of Aβ protein, wherein the portion of Aβ protein binds to ABAD and comprises the sequence of amino acid residues 1-20 of Aβ protein.

This invention further provides a composition of matter comprising a polypeptide consisting of a portion of Aβ protein comprising the sequence of amino acid residues 1-20 of Aβ protein, wherein the composition binds to ABAD. In the preferred embodiment of this composition, the Aβ protein is human Aβ protein. In another embodiment, the composition is further comprised by a pharmaceutically acceptable carrier.

This invention further provides a composition of matter comprising (a) a Tat protein operatively affixed to (b) a polypeptide consisting of a portion of Aβ protein comprising the sequence of amino acid residues 1-20 of Aβ protein, wherein the composition binds to ABAD. In the preferred embodiment of this composition, the Aβ protein is human Aβ protein. In another embodiment, the composition is further comprised by a pharmaceutically acceptable carrier.

This invention further provides a method for treating a subject afflicted with Alzheimer's disease comprising administering to the subject a therapeutically effective amount of an agent that inhibits binding between Aβ protein and ABAD in the subject's cells.

In the preferred embodiment of this method, the subject is human. In another embodiment, the cells are neuronal cells.

Determining a therapeutically effective amount of the instant polypeptides and compositions can be done based on animal data using routine computational methods. In one embodiment of the instant invention, the therapeutically effective amount of polypeptide or composition is between 0.01 and 1000 mg/kg body weight/day. In another embodiment, the therapeutically effective amount is between 0.25 and 50 mg/kg body weight/day. In a preferred embodiment, the therapeutically effective amount is between 1.0 and 10 mg/kg body weight/day.

In one embodiment of this method, the agent is a polypeptide consisting of a portion of ABAD, wherein the portion of ABAD binds to Aβ protein and comprises the sequence of amino acid residues 94-114 of ABAD. In another embodiment, the agent is a composition of matter comprising a polypeptide consisting of a portion of ABAD comprising the sequence of amino acid residues 94-114 of ABAD, wherein the composition binds to Aβ protein. In yet another embodiment, the agent is a polypeptide consisting of a portion of Aβ protein, wherein the portion of Aβ protein binds to ABAD and comprises the sequence of amino acid residues 1-20 of Aβ protein. In yet another embodiment, the agent is a composition of matter comprising a polypeptide consisting of a portion of Aβ protein comprising the sequence of amino acid residues 1-20 of Aβ protein, wherein the composition binds to ABAD.

This invention further provides a method for reducing free radical generation in a cell comprising introducing into the cell an agent that inhibits binding between Aβ protein and ABAD. In the preferred embodiment of this and other instant methods involving introducing an agent into a cell, the agent enters the cell's mitochondria once present in the cell's cytosol.

In one embodiment of this method, the cell is a neuronal cell.

In one embodiment of this method, the agent is a polypeptide consisting of a portion of ABAD, wherein the portion of ABAD binds to Aβ protein and comprises the sequence of amino acid residues 94-114 of ABAD. In another embodiment, the agent is a composition of matter comprising a polypeptide consisting of a portion of ABAD comprising the sequence of amino acid residues 94-114 of ABAD, wherein the composition binds to Aβ protein. In yet another embodiment, the agent is a polypeptide consisting of a portion of Aβ protein, wherein the portion of Aβ protein binds to ABAD and comprises the sequence of amino acid residues 1-20 of Aβ protein. In yet another embodiment, the agent is a composition of matter comprising a polypeptide consisting of a portion of Aβ protein comprising the sequence of amino acid residues 1-20 of Aβ protein, wherein the composition binds to ABAD.

This invention further provides a method for reducing DNA fragmentation in the cytosol of a cell comprising delivering into the cell an agent that inhibits binding between Aβ protein and ABAD.

In one embodiment of this method, the cell is a neuronal cell.

In one embodiment of this method, the agent is a polypeptide consisting of a portion of ABAD, wherein the portion of ABAD binds to Aβ protein and comprises the sequence of amino acid residues 94-114 of ABAD. In another embodiment, the agent is a composition of matter comprising a polypeptide consisting of a portion of ABAD comprising the sequence of amino acid residues 94-114 of ABAD, wherein the composition binds to Aβ protein. In yet another embodiment, the agent is a polypeptide consisting of a portion of Aβ protein, wherein the portion of Aβ protein binds to ABAD and comprises the sequence of amino acid residues 1-20 of Aβ protein. In yet another embodiment, the agent is a composition of matter comprising a polypeptide consisting of a portion of Aβ protein comprising the sequence of amino acid residues 1-20 of Aβ protein, wherein the composition binds to ABAD.

This invention further provides a method for reducing cytochrome c release from mitochondria in a cell comprising introducing into the cell an agent that inhibits binding between Aβ protein and ABAD.

In one embodiment of this method, the cell is a neuronal cell.

In one embodiment of this method, the agent is a polypeptide consisting of a portion of ABAD, wherein the portion of ABAD binds to Aβ protein and comprises the sequence of amino acid residues 94-114 of ABAD. In another embodiment, the agent is a composition of matter comprising a polypeptide consisting of a portion of ABAD comprising the sequence of amino acid residues 94-114 of ABAD, wherein the composition binds to Aβ protein. In yet another embodiment, the agent is a polypeptide consisting of a portion of Aβ protein, wherein the portion of Aβ protein binds to ABAD and comprises the sequence of amino acid residues 1-20 of Aβ protein. In yet another embodiment, the agent is a composition of matter comprising a polypeptide consisting of a portion of Aβ protein comprising the sequence of amino acid residues 1-20 of Aβ protein, wherein the composition binds to ABAD.

This invention further provides a method for preserving cell viability by reducing LDH release from a cell comprising introducing into the cell an agent that inhibits binding between Aβ protein and ABAD.

In one embodiment of this method, the cell is a neuronal cell.

In one embodiment of this method, the agent is a polypeptide consisting of a portion of ABAD, wherein the portion of ABAD binds to Aβ protein and comprises the sequence of amino acid residues 94-114 of ABAD. In another embodiment, the agent is a composition of matter comprising a polypeptide consisting of a portion of ABAD comprising the sequence of amino acid residues 94-114 of ABAD, wherein the composition binds to Aβ protein. In yet another embodiment, the agent is a polypeptide consisting of a portion of Aβ protein, wherein the portion of Aβ protein binds to ABAD and comprises the sequence of amino acid residues 1-20 of Aβ protein. In yet another embodiment, the agent is a composition of matter comprising a polypeptide consisting of a portion of Aβ protein comprising the sequence of amino acid residues 1-20 of Aβ protein, wherein the composition binds to ABAD.

This invention further provides an article of manufacture comprising a packaging material having therein a polypeptide consisting of a portion of ABAD, wherein the portion of ABAD binds to Aβ protein and comprises the sequence of amino acid residues 94-114 of ABAD, and wherein the packaging material has affixed thereto a label indicating a use for the polypeptide for treating a subject afflicted with Alzheimer's disease. In the preferred embodiment of this article, the subject is a human.

This invention further provides an article of manufacture comprising a packaging material having therein a composition of matter comprising a polypeptide consisting of a portion of ABAD comprising the sequence of amino acid residues 94-114 of ABAD, wherein the composition binds to Aβ protein, and wherein the packaging material has affixed thereto a label indicating a use for the composition for treating a subject afflicted with Alzheimer's disease. In the preferred embodiment of this article, the subject is a human.

This invention further provides an article of manufacture comprising a packaging material having therein a polypeptide consisting of a portion of Aβ protein, wherein the portion of Aβ protein binds to ABAD and comprises the sequence of amino acid residues 1-20 of Aβ protein, and wherein the packaging material has affixed thereto a label indicating a use for the polypeptide for treating a subject afflicted with Alzheimer's disease. In the preferred embodiment of this article, the subject is a human.

This invention further provides an article of manufacture comprising a packaging material having therein a composition of matter comprising a polypeptide consisting of a portion of Aβ protein comprising the sequence of amino acid residues 1-20 of Aβ protein, wherein the composition binds to ABAD, and wherein the packaging material has affixed thereto a label indicating a use for the composition for treating a subject afflicted with Alzheimer's disease. In the preferred embodiment of this article, the subject is a human.

This invention further provides a method for determining whether an agent inhibits the binding of Aβ protein to ABAD, which comprises: (a) admixing (i) a polypeptide consisting of a portion of ABAD, wherein the portion of ABAD binds to Aβ protein and comprises the sequence of amino acid residues 94-114 of ABAD, (ii) Aβ protein, and (iii) the agent, under conditions which would permit binding of the polypeptide and Aβ protein in the absence of the agent; (b) determining the amount of polypeptide bound to Aβ protein in step (a); and (c) comparing the amount of bound polypeptide determined in step (b) with the amount determined in the absence of the agent, whereby a lower amount of binding in the presence of the agent indicates that the agent inhibits the binding of Aβ protein to ABAD.

In one embodiment of the instant assays, as well as the instant polypeptides, compositions, therapeutic methods and other methods, the portion of ABAD and/or of Aβ protein is unmodified, i.e., it contains no amino acid residue derivatives and its amino acid residues are bound by peptide bonds. In another embodiment, the portion of ABAD and/or of Aβ protein contains at least one amino acid residue derivative (e.g., a residue having a non-naturally occurring side chain) and/or contains at least one non-peptide bond joining two amino acid residues. These portions can also include modifications such as glycosylation, lipid attachment, sulfation, hydroxylation, and ADP-ribosylation.

This invention further provides a method for determining whether an agent inhibits the binding of Aβ protein to ABAD, which comprises: (a) admixing (i) a polypeptide consisting of a portion of Aβ protein, wherein the portion of Aβ protein binds to ABAD and comprises the sequence of amino acid residues 1-20 of Aβ protein, (ii) ABAD, and (iii) the agent, under conditions which would permit binding of the polypeptide and ABAD in the absence of the agent; (b) determining the amount of polypeptide bound to ABAD in step (a); and (c) comparing the amount of bound polypeptide determined in step (b) with the amount determined in the absence of the agent, whereby a lower amount of binding in the presence of the agent indicates that the agent inhibits the binding of Aβ protein to ABAD.

This invention further provides a method for determining whether an agent inhibits the binding of Aβ protein to ABAD, which comprises: (a) admixing (i) a polypeptide consisting of a portion of ARAB, wherein the portion of ABAD binds to Aβ protein and comprises the sequence of amino acid residues 94-114 of ARAB, (ii) a polypeptide consisting of a portion of Aβ protein, wherein the portion of Aβ protein binds to ABAD and comprises the sequence of amino acid residues 1-20 of Aβ protein, and (iii) the agent, under conditions which would permit binding of the portion of ABAD and the portion of A protein in the absence of the agent; (b) determining the amount of portion of ARAB bound to portion of A protein in step (a); and (c) comparing the amount of the bound portion of ARAB determined in step (b) with the amount determined in the absence of the agent, whereby a lower amount of binding in the presence of the agent indicates that the agent inhibits the binding of Aβ protein to ABAD.

This invention is illustrated in the Experimental Details section which follows. This section is set forth to aid in an understanding of the invention but is not intended to, and should not be construed to, limit in any way the invention set forth in the claims which follow.

Experimental Details

Methods

Immunoprecipitation/Immunoblotting.

Human brain tissues from AD patients and age-matched non-demented controls (N=3 in each case) were homogenized in Tris buffer (10 mM Tris, 0.1 M NaCl, 1 mM EDTA, 100 µg/ml PMSF, 1 µg/ml aprotinin), immunoprecipitated with rabbit anti-Aβ IgG (3 µl/500 µg protein) at 4° C. overnight, and Western blotting was done with mouse anti-ABAD IgG (1:1000). Immunoprecipitation was performed on incubation of crude extracts (500 µg) from cerebral cortex with anti-Aβ antibody followed by immunoblotting with anti-ABAD IgG. Peroxidase-conjugated goat anti-mouse IgG (specific for heavy chain, Jackson Lab) was used as a secondary antibody. Electrophoresis was performed with 12% Tris-Glycine SDS-PAGE. Results shown are representative of the 3 patients in each group. The same methodology was employed for immunoprecipitation/immunoblotting studies of mitochondria derived from brains of Tg mAPP/ABAD mice.

Transgenic (Tg) Mice overexpressing a mutant human form of amyloid precursor protein (mAPP), the latter a minigene encoding hAPP695, 751 and hAPP770 bearing V717I/F, K670M, N671L; J-20 line) in the C57BL6 background were provided by Dr. Lennart Mucke (6). The latter are termed Tg mAPP mice (>N10 in the C57BL/6 strain). Tg ABAD mice (N8 in the C57BL/6 strain), which overexpress ABAD under control of the PDGF B-chain promoter have described previously (7). Tg mAPP and Tg ABAD animals were crossed to generated Tg mAPP/ABAD, Tg mAPP, Tg ABAD and nontransgenic littermates. Offspring were identified by PCR using primers for specific for each transgene.

Isolation of Mitochondria.

Brain tissue in isolation buffer (20 mM Hepes at pH 7.2 and 1 mM EDTA) was subjected to 10 strokes of a glass teflon potter homogenizer. The homogenate was centrifuged at 1,700 rpm for 6 min at 4° C. The resulting supernatant was then centrifuged at 5000 g for 10 min. The pellet was resuspended in isolation buffer, and layered on a Ficoll gradient generated from 5 ml of 11% Ficoll and 3 ml of 7.5% Ficoll and centrifuged in an AH-628 rotor at 79,000 g for 30 minutes. The pellet was resuspended again in isolation buffer, incubated with fresh digitonin (1.25 mg/100 mg brain tissues) for 15 min on ice, and then centrifuged at 6,500 rpm for 10 min. The resulting new pellet, containing highly purified mitochondria, was washed with 0.2% BSA and resuspended in isolation buffer.

Crystallography.

Expression and purification of human ABAD was performed as described (3,7). For crystallization, ABAD was concentrated to 10 mg/ml in 25 mM MES at pH 6.0, 0.1 M NaCl and 5 mM DTT and mixed with 5 mM NAD and 3- to 4-fold molar excess of Aβ (residues 1-40; Biosource, CA). The mixture was crystallized by vapor diffusion at 22° C. using a precipitant solution containing 0.1 M MES at pH 6.0, 2.5 M NaCl, 5 mM benzamidine and 5 mM NAD. Diffraction data were collected at the COM-CAT beamline of Advanced Photon Source and processed with the HKL package (23). The structure was determined by molecular replacement calculations in the program Replace (24, 25) using the rat ABAD structure as a search model. Limited six-dimensional search and a high large term cutoff (2.0) were used in the structure determination. Retrospectively, these strategies were crucial in overcoming the hurdle provided by the high symmetry of the space group and the large conformational differences between rat ABAD and human Aβ-bound ABAD structures. Refinement was carried out by the simulated annealing protocol in CNS (26). Model building was performed in program (27, 28). The final atomic model contains residues 6-94, 114-207 and 229-253.

Studies with ABAD-Derived Peptides.

ABAD decoy peptide (ABAD-DP, residues 92-120, with a sequence of Ala-Gly-Ile-Ala-Val-Ala-Ser-Lys-Thr-Tyr-Asn-Leu-Lys-Lys-Gly-Gln-Thr-His-Thr-Leu-Glu-Asp-Phe-Gln-Arg-Val-Leu-Asp-Val; SEQ ID NO. 3) and ABAD reverse peptide (ABAD-RP, residues 120-92) were synthesized by Biotechnology Lab at Yale University. For binding studies, ABAD was immobilized on CM5 sensor chip (29). As indicated, Aβ(1-40) or Aβ(1-42) alone or with either ABAD-DP or ABAD-RP (range of concentrations) was injected at a flow rate of 30 µl/min for 2 min at 25° C. using Biacore X (Pharmacia). The reaction/binding buffer contained 50 mM Hepes at pH 7.4, 0.15 M NaCl, 1 mM EDTA, and 0.005% Tween 20. Data analysis was performed using Biacore X biosensor system (Uppsala, Sweden) and BIA evaluation 3.0 software (Biacore, Sweden). Response data are plotted in Resonance Units versus ABAD peptide concentrations (nM), and were fit to a one-site model for competitive inhibition to obtain the $K_i$.

The Effect of ABAD-DP on Cytochrome C Release.

Primary cortical neurons (4 day) from mice of each of the genotypes were cultured. The effect of ABAD-DP on cytochrome c release was studied by pre-treating cultures with ABAD-DP (10 µM) or ABAD-RP (10 µM) for 60 minutes, followed by incubation with Aβ(1-42; 1 µM) for nonTg and Tg ABAD mice. After 24 hours at 37° C., cytosolic cytochrome c was determined by the following procedure. Briefly, cells plated on 100 mm dishes were washed with cold PBS, scraped using a rubber policeman, and collected by centrifugation at 300 g for 5 min at 4° C. The pellet was resuspended in 400 µl of lysis buffer containing 50 mM Tris at pH 7.4, 1 mM EDTA, 1 mM EGTA, 250 mM sucrose, 2 µg/ml leupeptin, 1 mM PMSF, and 1 fig/ml pepstatin A and disrupted with strokes of a Dounce homogenizes Cytosol and membrane fractions were separated by centrifugation at 105,000 g for 1 hour at 4° C. (11). The resulting pellets were resuspended in 50 µl of lysis buffer and supernatants were concentrated to 20 µl. The protein content of each fraction was determined by the BioRad DC protein assay (BioRad Laboratories, Hercules, Calif.). Samples (40 μg/lane) were subjected to 12% SDS-PAGE, followed by immunoblotting using anti-cytochrome c antibody (1:500) (Phamergen).

The Effect of ABAD-DP on Intracellular Generation of ROS.

Studies were also performed to determine the effect of ABAD-DP on intracellular generation of ROS by neurons from Tg mice using DCFDA fluorescent probe (31, 32). Cells plated on 100 mm dishes were washed with Hanks balanced saline solution, incubated with 0.05% trypsin-EDTA containing 1 μM DCFDA for 25 minutes and collected by centrifugation at 300 g for 5 min at room temperature. The pellet was resuspended in 1.5 ml Earle's balanced saline solution and exposed to Aβ (1-42, 4 μg/ml) for 5 minutes. Fluorescence was measured with excitation at 490 nm and emission at 530 nm using a FluoroMax-2 spectrofluorometer (Jobin Yvon Inc., Edison, N.J.). Other studies investigated the effect of ABAD-DP on Aβ-induced and spontaneous DNA fragmentation (Cell Death Detection ELISA$^{PLUS}$, Roche Diagnostics Co. Indianapolis, Ind.) and LDH release (Sigma).

EPR Spectra were recorded on frozen brain tissues in liquid nitrogen using a quartz dewar at X-band. Brain tissue was extruded in the form of a cylinder with 5 mm diameter at room temperature and quickly frozen in liquid nitrogen. The measurements were performed on frozen intact tissue. No processing (grinding) was done on the frozen sample to avoid artifacts. The spectrometer was set at a frequency of 9.561 GHz, a modulation amplitude of 2.5 G and a microwave power of 1 mW. Spectral acquisitions were performed for 10 min on each sample.

The Radial-Arm Water Maze Task ($p<0.05$; $N=7$-$8$) was performed as previously described. Investigators were blinded to mouse genotypes (14). Mice had to find a platform hidden beneath the water surface at the end of one of the six arms. The four groups of animals under study in our behavioral experiments were littermates. This breeding strategy and the C57BL/6 background were employed to enhance the reproducibility and reliability of our results in the radial arm water maze, based on work of other investigators. Time to reach the platform and speed of swimming were recorded and analyzed with a video-tracking system (HVS-2020, HVS Image, UK).

Results

Figure 6:
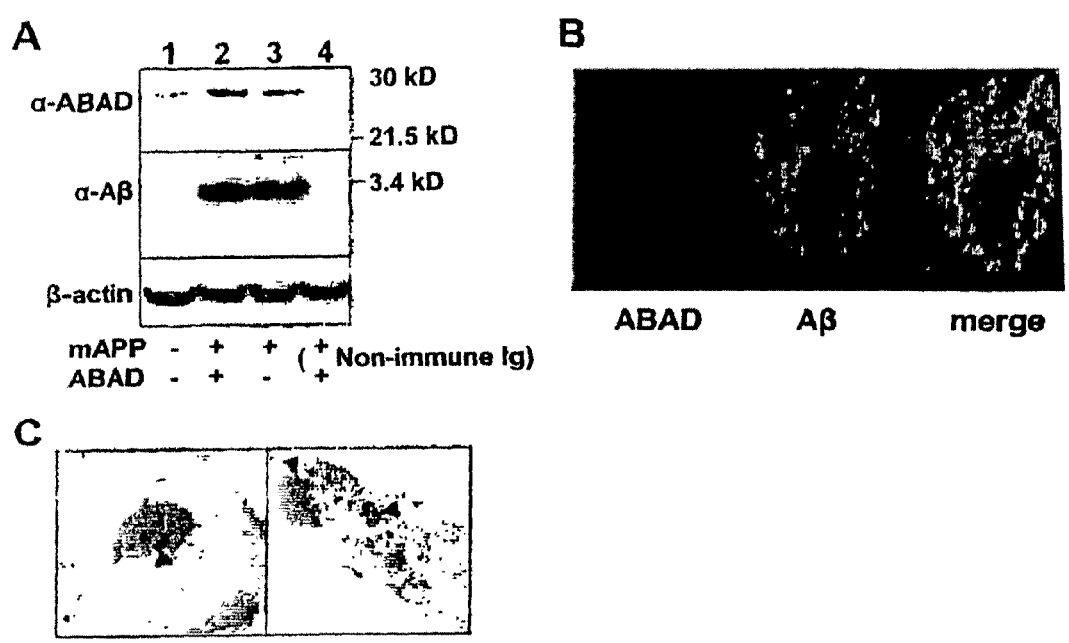
FIG. 6. Demonstration of ABAD-Aβ complex in brains of Tg mAPP/ABAD mice. A, Co-immunoprecipitation of ABAD and Aβ from mitochondria of transgenic mice. Mitchondrial fractions (500 μg) from cerebral cortex of nonTg, Tg mAPP and Tg mAPP/ABAD mice were immunoprecipitated with mouse anti-Afi IgG (6E10; 8 μg/ml), or nonimmune IgG (8 μg/ml) at 4° C. overnight followed by Western blotting wi$^+$ mouse anti-ABAD (1:10,000). The middle panel snows total input protein reprobed with anti-AR antibody (6E 10). Lower panel shows immunoblotting of β-actin for crude extracts from mouse brains. B, Co-localization of ABAD and Aβ in the brain of a Tg mAPP/ABAD mouse using confocal microscopy with antibodies to ABAD and Aβ (color not shown) (magnification 300-fold). C, Colocalization of ABAD and Aβ in mitochondria of brains from Tg mAPP/ABAD mouse using electron microscopy. Double immunogold staining was performed with rabbit anti-Aβ IgG and mouse anti-ABAD IgG followed by goat anti-rabbit IgG conjugated to 12 nm gold particles (for Aβ1-42) and goat anti-mouse IgG conjugated to 18 nM gold particles (for ABAD). Arrowheads depict gold particles localizing ABAD antigen. The smaller gold particles represent sites of localization of Aβ.

It was speculated that interaction of Aβ with ABAD might induce mitochondrial dysfunction. However, since it had not been established that intracellular Aβ can access mitochondria, it was essential to determine whether ABAD and Aβ interact in pathophysiologically relevant settings. To address this directly, ABAD-Aβ complex was detected in AD brains by immunoprecipitation of cortical protein extracts using anti-Aβ followed by immunoblotting with anti-ABAD IgG (FIG. 1A). Age-matched non-demented brain displayed very little ABAD-Aβ complex. Substitution of nonimmune IgG for specific antibodies prevented appearance of the band (not shown). Since cellular and mitochondrial integrity may start to deteriorate soon after death, allowing non-physiological interactions to occur, mitochondria were isolated from the cerebral cortex of 12 month-old mice expressing mAPP (6), ABAD (7) or both, driven by the PDGF B-chain promoter. The purity of mitochondrial preparations was confirmed by enrichment of Cox IV (cytochrome c oxidase IV), and relative absence of lysosomal (cathepsin D) and endoplasmic reticulum (PDI, protein disulfide isomerase) markers (FIG. 16). ABAD-Aβ complex was evident in the mitochondria of both transgenic (Tg) mAPP and Tg mAPP/ABAD mice (FIG. 6A). Similar bands were only present at very low levels in samples from age- and strain-matched nonTg littermates or when nonimmune IgG replaced specific antibodies.

Confocal microscopy was used to confirm mitochondrial co-localization and interaction of ABAD and Aβ. In the cerebral cortex of AD patients, images of anti-ABAD and anti-Aβ (color not shown), detecting endogenous ABAD and Aβ, extensively co-localize (FIG. 1C). Similarly, in the cerebral cortex of Tg mAPP/ABAD mice, there is extensive overlap of immunoreactive ABAD and Aβ (FIG. 6B). Because ABAD is mainly localized to mitochondria, as shown by the overlap of anti-ABAD and anti-VDAC (voltage-dependent anion channel) images (color not shown) (FIG. 1D), these data demonstrate that Aβ is also present in the mitochondria of AD patients. Immunogold electron microscopy using gold-conjugated antibody systems provided further evidence for the presence of ABAD and Aβ within mitochondria (for ABAD, 18 nm gold particles and for Aβ, 12 nm gold particles). The two different sizes of gold particles are concentrated in the mitochondria of brains from a patient with AD (FIG. 1E) and from Tg mAPP/ABAD mice (FIG. 6C). Taken together, these microscopic and immunoprecipitation data demonstrate the formation of ABAD-Aβ complex within mitochondria in vivo.

Figure 2:
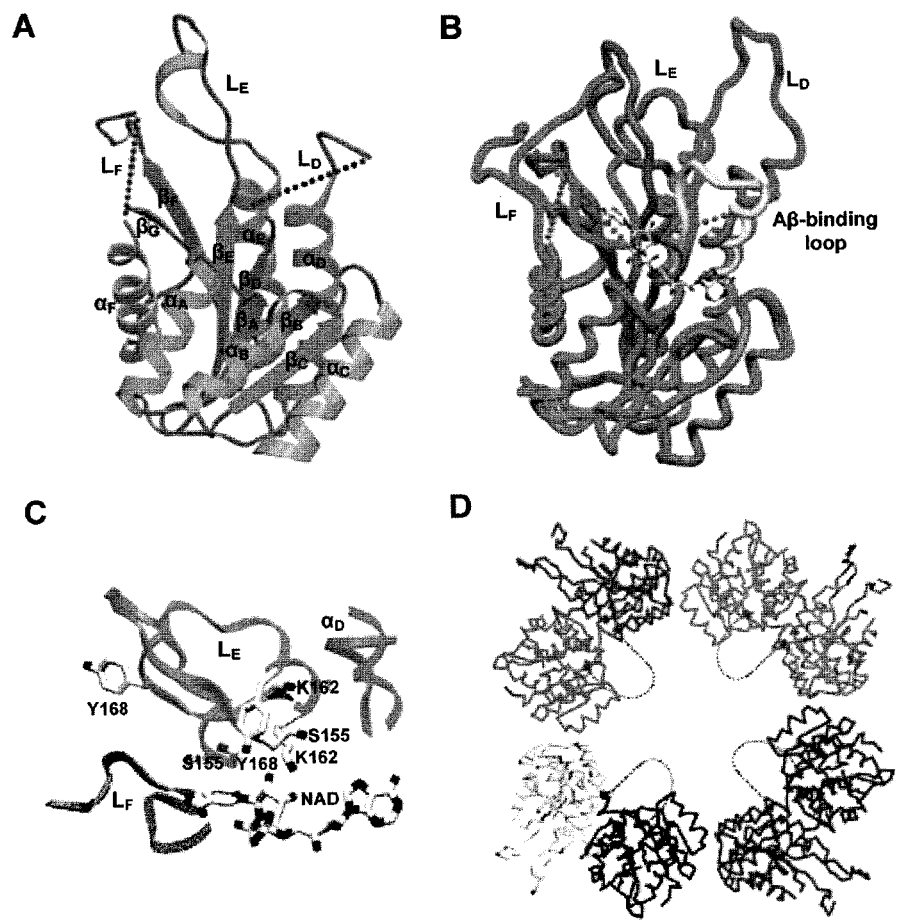
FIG. 2. Crystal structure of Aβ-bound human ABAD. (A) A ribbon diagram with labeled secondary structures and the $L_D$, $L_E$ and $L_F$ loops. (B) Superposition of Aβ-bound human ABAD (magenta) and rat ABAD in complex with NAD (cyan). The $L_D$ loop of 3α-hydroxysteroid dehydrogenase (3α-HSD) (PDB code 1FJH) is shown in yellow. The proposed Aβ-binding loop is indicated. (C) Superposition of the active sites of Aβ-bound human ABAD (magenta) and rat ABAD (cyan), showing distortion of the NAD binding site and the catalytic triad S155, K162 and Y168. (D) A section of the crystal packing interactions, showing the large solvent channels. Each ABAD molecule is shown in a different color. The ordered ends of the $L_D$ loop, residues 94 and 114, are marked as red and blue balls, respectively, and the hypothetical loops are shown in magenta as dotted curvy lines.

To determine the structural basis of the ABAD-Aβ interaction, human ABAD was crystallized and its structure was determined, in the presence of NAD and a molar excess of Aβ, at 2.3 Å resolution (FIG. 2A, Table 2). Unexpectedly, NAD is not bound to ABAD in the crystal structure. Under the crystallization condition, Aβ inhibits ABAD activity, though, in the absence of Aβ, ABAD displays normal activity. This suggests that Aβ prevents NAD binding in the crystal structure, which may be the molecular basis for its inhibition of ABAD activity.

Figure 7:
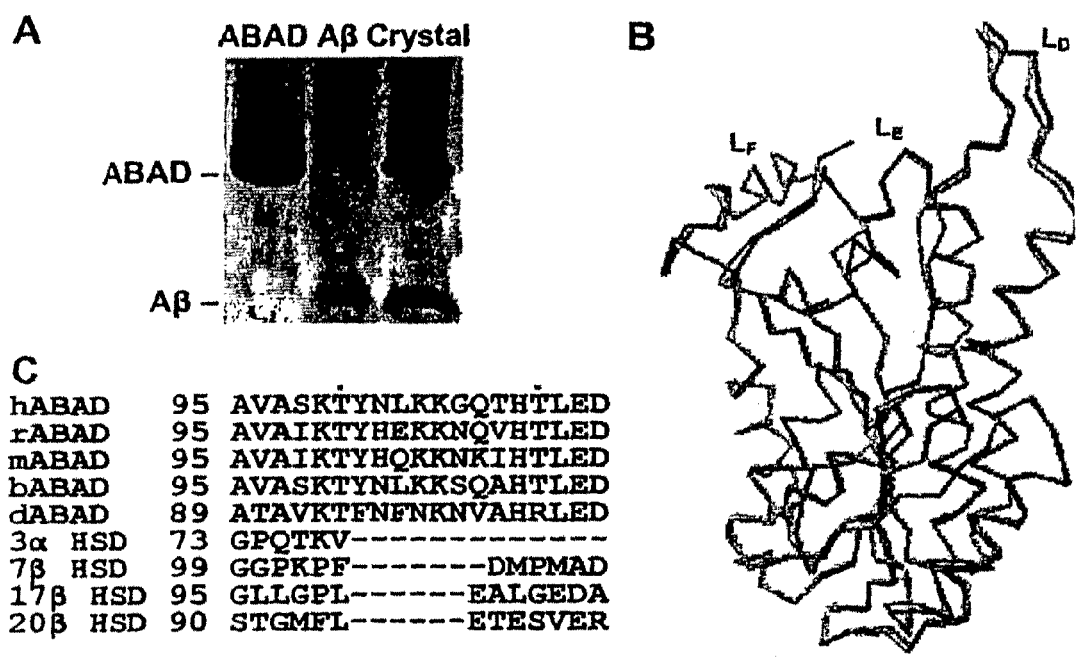
FIG. 7. A, SDS-PAGE of washed and dissolved crystals of human ABAD and Aβ. Lanes from left to right: ABAD standard, Aβ (1-40) standard and dissolved crystals. B, Superposition of rat ABAD in complex with NAD and human ABAD in complex with NAD and an inhibitor (color not shown). The $L_D$ and $L_E$ loops are very similar. The $L_F$ loop is ordered in the human structure but disordered in the rat structure. C, Sequence alignment of the disordered part of the $L_D$ loop (residues 95-113) among human, rat, mouse, bovine and *Drosophila* ABAD and several HSDs, members of the SDRs, showing the insertion in ABAD relative to other HSDs (SEQ ID NOS. 6-14, respectively).

SDS-PAGE and amino terminal sequencing of washed and dissolved crystals showed that both ABAD and Aβ are present in the crystals (FIG. 7A). However, no electron density is observed for Aβ, suggesting that Aβ itself and the region of ABAD that binds to Aβ must be disordered in the crystal. To exclude the possibility that Aβ interacts with ABAD non-specifically, additional experiments were performed, which showed that other amyloid species such as a prion-derived peptide and amylin did not bind to ABAD. In addition, Aβ(1-42), Aβ(1-40) and Aβ(1-20) demonstrated dose-dependent binding, whereas Aβ(25-35) showed no specific binding (Table 3).

Comparison of the Aβ-bound ABAD structure with the rat ABAD structure in complex with NAD (B) and the human ABAD structure in complex with NAD and a small molecule inhibitor (9) shows that the Aβ-bound ABAD displays significant distortion of the NAD-binding pocket and the catalytic triad (FIG. 2B, 2C, 7B). The majority of the $L_D$ loop, the beginning of the following $α_D$ helix, and the latter part of the $L_F$ loop of human ABAD are disordered. While the $L_E$ loop is ordered, the conformation of the loop and the beginning of the following $α_E$ helix is significantly different from the structure without Aβ.

In the absence of substrate, the $L_F$ loop is also disordered in the rat ABAD structure in complex with NAD, while the $L_D$ loop region is well ordered, suggesting that Aβ binding may have influenced the $L_D$ loop dynamics and conformation. In addition, within the NAD-dependent short-chain dehydrogenase/reductase (SDR) superfamily, the $L_D$ loop of ABAD from different species contains a unique insertion that is absent in all other SDRs (FIG. 7C). Because ABAD is the only SDR that has been observed to bind Aβ, it was hypothesized that the $L_D$ loop may be a recognition site for Aβ.

Inspection of crystal packing showed that the ordered ends of the $L_D$ loop point into interconnected huge solvent channels with estimated dimensions of 70 Å (FIG. 2D). It is estimated that the ordered part of the crystal only occupies about 30% of the total crystal volume. Sufficient space is therefore available for the disordered loops and the bound Aβ, which could drift freely in the large solvent channels in the crystal to cause disorder or nonspecifically hind and clog the active site region to inactivate the enzyme.

Figure 3:
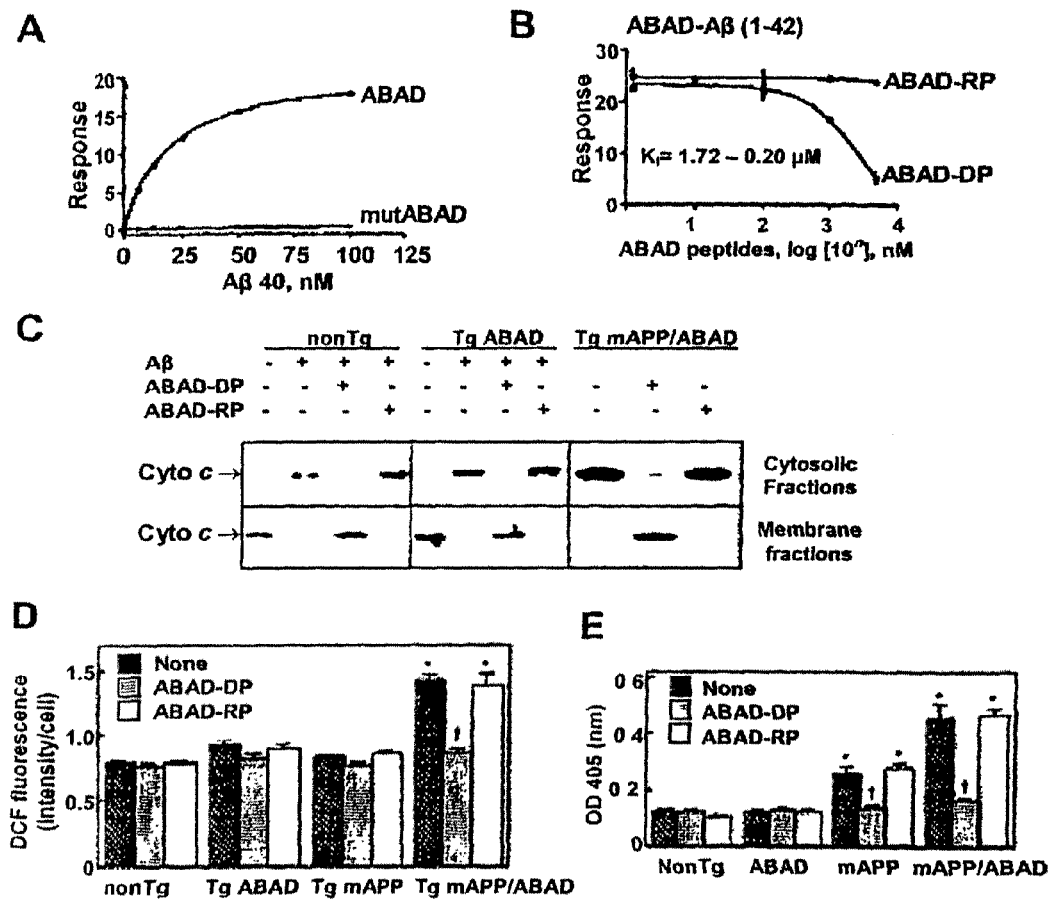
FIG. 3. Biochemical and functional effects of ABAD-DP. (A-B) Effect of mutations in the $L_D$ loop of ABAD on Aβ binding (A) and inhibition of ABAD-Aβ interaction by ABAD-DP (B), measured by surface plasmon resonance. ABAD was immobilized on the sensor chips; for A, wild-type or mutant (S98A, K99A, Y101A) ABAD was immobilized and for B, wild-type was used. For A, the mobile (injected) phase was Aβ (1-40) and for B, the mobile phase was a mixture of Aβ (1-42) and either ABAD-DP or ABAD-RP (range of concentrations). (C) Inhibition of Aβ-induced and spontaneous cytochrome c release from mitochondrial or membrane fraction by ABAD-DP in cultured neurons. (D-E) Inhibition of ROS generation (D) and DNA fragmentation (E) by ABAD-DP. *P<0.05, versus nonTg cells; P<0.05, versus without ABAD-DP treatment.

To test the idea that the $L_D$ loop is important in Aβ interaction, structure-based mutational analyses were performed (Table 1). Binding studies using Aβ and GST-ABAD truncation mutants showed that the amino terminal portion of ABAD (residues 1-158) is responsible for Aβ interaction. Site-directed mutagenesis within and beyond the disordered $L_D$ loop region (residues 95-113) specifically located two stretches of ABAD residues important for Aβ binding, residues S98-Y101 and residues T108-T110. An ABAD mutant bearing S98A, K99A and Y101A mutations exhibited no specific interaction to Aβ in a surface plasmon resonance experiment, although wild-type ABAD displayed dose-dependent interaction with Aβ (FIG. 3A).

To determine whether the $L_D$ loop is sufficient for Aβ interaction, a peptide was synthesized encompassing this region (residues 92-120) of human ABAD (termed ABAD decoy peptide, or ABAD-DP) and its ability to inhibit the interaction of intact ABAD with Aβ using surface plasmon resonance was tested (FIG. 38). ABAD-DP inhibited binding of Aβ (1-40) (FIG. 8A) and Aβ (1-42) (FIG. 38) to immobilized intact ABAD with inhibitory constants of 4.9 and 1.7 μM, respectively. On the other hand, a peptide of the reverse sequence (residues 120-92, termed ABAD reversed peptide, or ABAD-RP) was completely inactive. These competitive binding studies confirmed that the $L_D$ region alone could mediate Aβ binding, although it may not be the exclusive site.

To develop a specific inhibitor of the ABAD-Aβ interaction in cultured neurons, the cell-membrane transduction domain of the human immunodeficiency virus-type 1 (HIV) Tat protein (10,11) was added to ABAD-DP and ABAD-RP (thereby enabling the peptides to cross cell membranes). Cytochrome c release from mitochondria was used as a marker of Aβ-induced cellular stress and apoptosis. While cultured wild-type cortical neurons exposed to Aβ(1-42) suffered loss of cytochrome c from the mitochondrial or membrane fraction to the cytosol fraction, pre-incubation of the cells with ABAD-DP, but not with ABAD-RP, largely prevented Aβ-induced cytochrome c release (FIG. 3C). Similarly, ABAD-DP also protected against Aβ-induced mitochondrial cytochrome c release in neurons from Tg ABAD mice, although these neurons displayed enhanced cytochrome c release compared with nonTg mice. Furthermore, pre-treatment with ABAD-DP, but not with ABAD-RP, dramatically reduced spontaneous loss of cytochrome c from the mitochondrial/membrane fraction of cultured neurons derived from Tg mAPP/ABAD mice.

Figure 8:
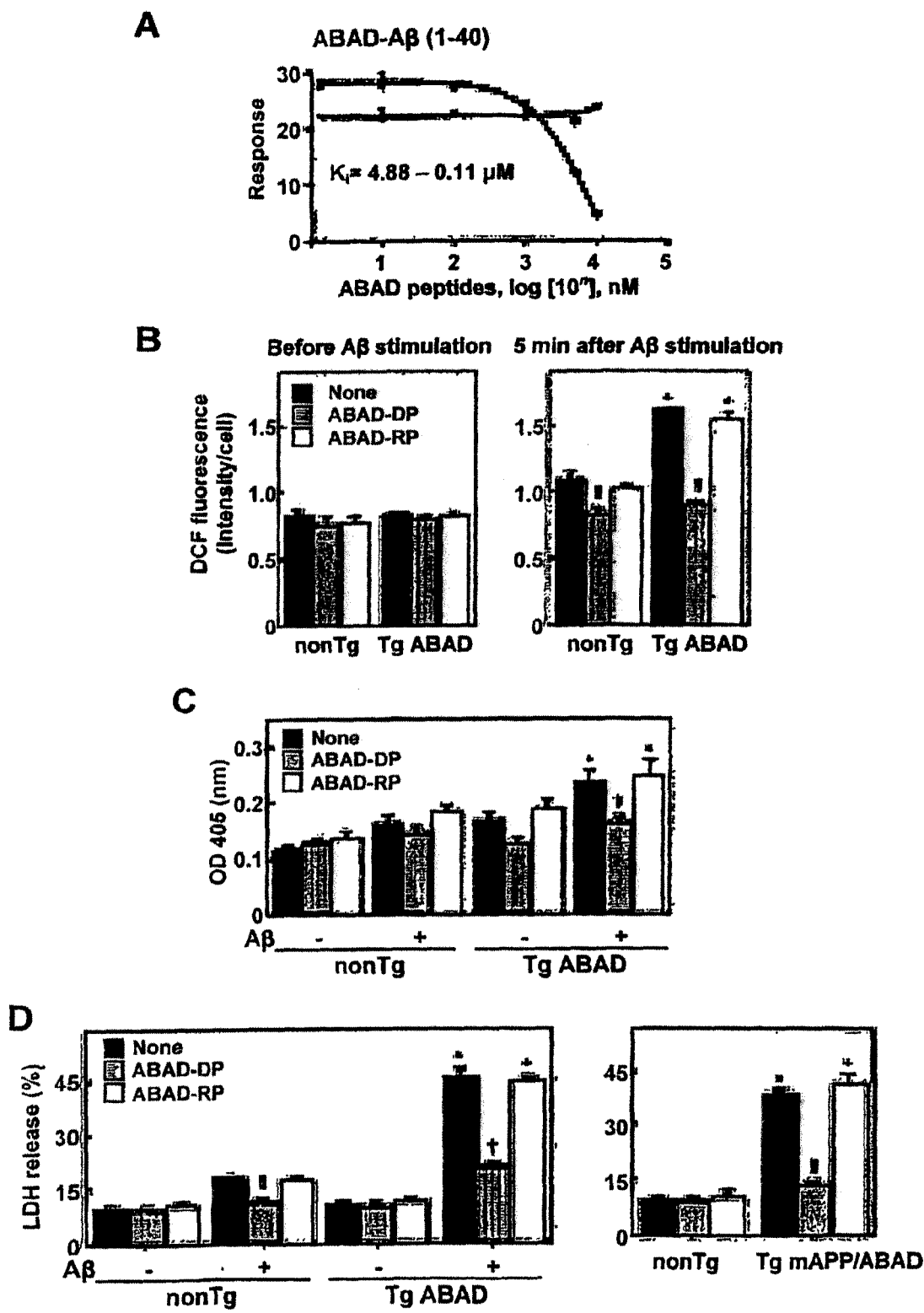
FIG. 8. A, Inhibition of ABAD-Aβ (1-40) interaction by ABAD-DP. ABAD was immobilized on the sensor chip of the Biacore and Aβ (1-40), in the presence of the indicated concentrations of ABAD-DP or ABAD-RP, was in the mobile phase. Response data are plotted in Resonance Units versus ABAD peptide concentrations (nM). B-D, Inhibition of Aβ-induced generation of ROS (B), DNA fragmentation (C) and LDH release (D) by ABAD-DP, but not by ABAD-RP. For inhibition by ABAD peptides, cells were pre-incubated with ABAD-DP or ABAD-RP (10 μM) for 60 min before Aβ treatment. *P<0.05, versus nonTg cells; $^+$P<0.05, versus without ABAD-DP treatment.

The protective effects of cell permeable ABAD-DP are consistent with the hypothesis that the ABAD-Aβ interaction causes mitochondrial stress and apoptosis. Since mitochondria are the principal sites of generation of reactive oxygen species (ROS) under physiologic conditions, and Aβ is known to trigger oxidative stress, we tested whether the protection from Aβ-induced cytotoxicity by ABAD-DP is accompanied by attenuated generation of ROS. Cultured neurons loaded with a probe for ROS, dichlorofluorescin diacetate (DCFDA), demonstrated fluorescence on exposure to Aβ, a phenomenon accentuated in neurons from Tg ABAD mice compared with nonTg littermates (FIG. 8B). Pre-treatment with ABAD-DP virtually completely suppressed fluorescence in DCFDA-loaded and Aβ-exposed neurons, from both nonTg and Tg ABAD animals (FIG. 8B). In contrast, there was no effect exerted by ABAD-RP. Furthermore, spontaneous generation of ROS by cultured neurons from Tg mAPP/ABAD mice was suppressed by pre-treatment with ABAD-DP, not ABAD-RP (FIG. 3D). Linkage between Aβ-ABAD-induced generation of ROS, and subsequent DNA fragmentation (FIG. 3E) and LDH release (FIG. 8D) was shown in cultured neurons from Tg mAPP/ABAD mice. Similarly, cultured neurons from Tg ABAD mice exposed to Aβ display subsequent DNA fragmentation (FIG. 8C), and LDH release (FIG. 8D). In each case, pretreatment with ABAD-DP, not ABAD-RP, attenuated cytotoxicity.

Figure 4:
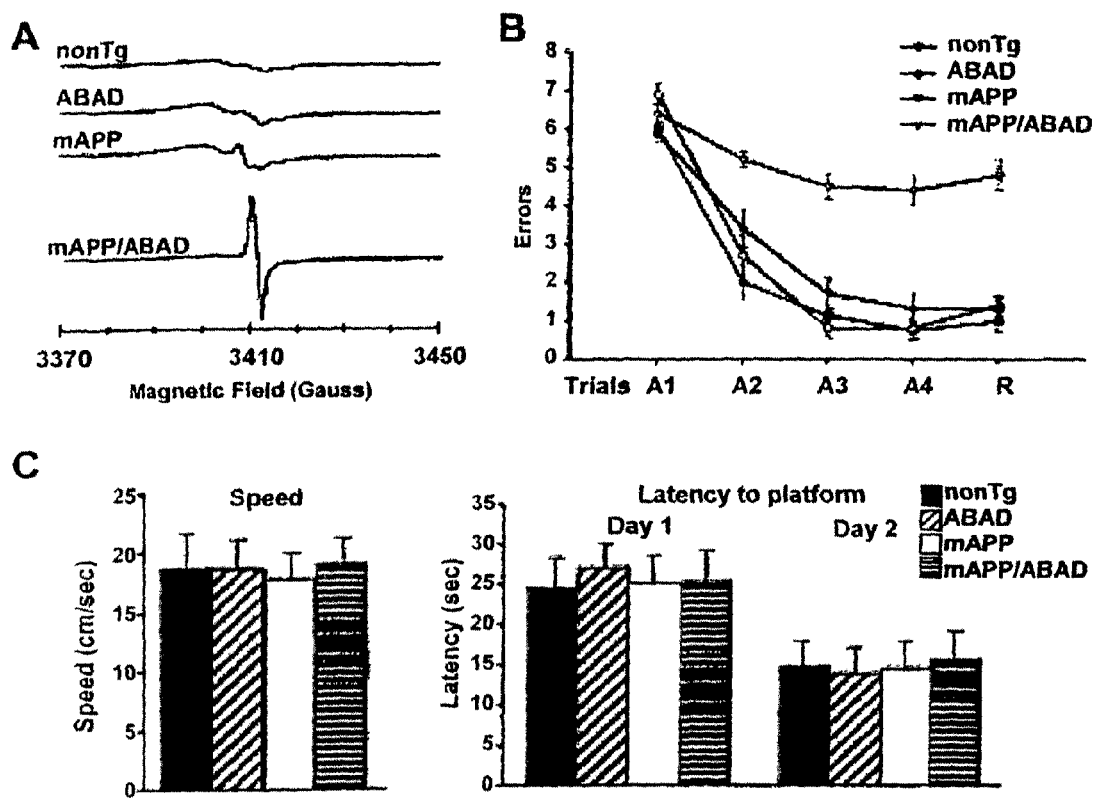
FIG. 4. Generation of free radicals and spatial learning and memory deficit in Tg mAPP/ABAD mice. (A) Generation of free radicals in Tg mAPP/ABAD mouse brains, shown by the sharp peak at 3410 Gauss in an EPR spectrum. The amplitude of the spectra for Tg mAPP, Tg ABAD and nonTg animals has been increased by 10-fold to display the spectra, which showed only low level changes. (B) Spatial learning is abnormal in 4.5-5 month old Tg mAPP/ABAD mice tested in the radial-arm water maze (P<0.05; N=7-8). (C) All groups (N=7-8) show similar speed and latency to find a visible platform.
Figure 5:
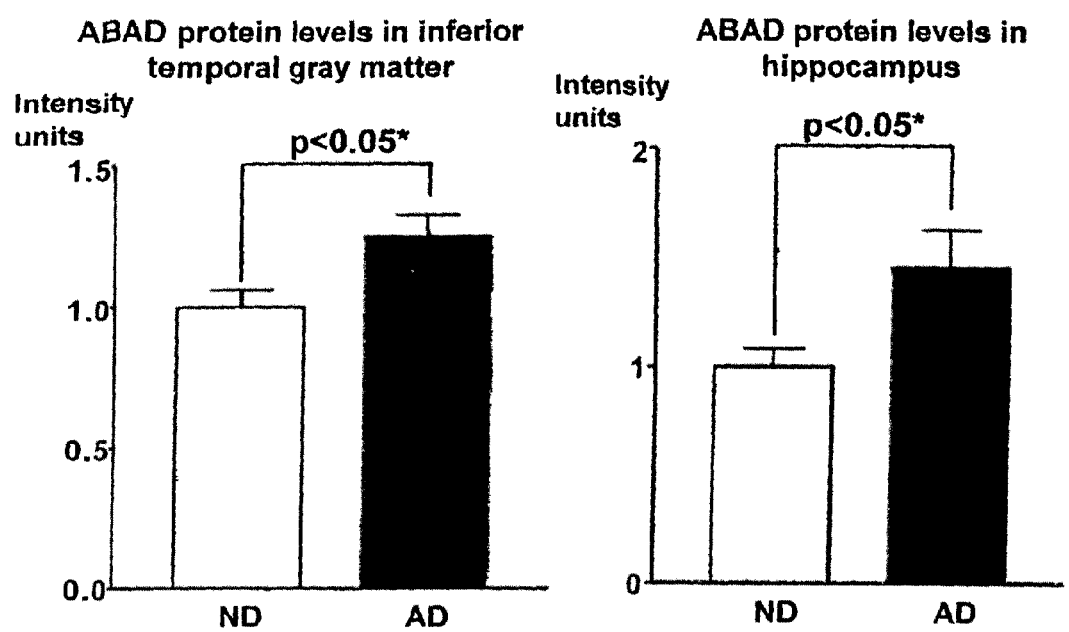
FIG. 5. Increased expression of ABAD in AD brains (n=19) as compared with age-matched controls (n=15). Brains from age-matched, pathologically confirmed 19 patient with AD (means+age 85.5+2.07), and 15 non-demented (ND) patients (means+age 82.07+1.465) were harvested according to the rapid autopsy procedure developed at Sun Health Institute (postmortem time 2.7±0.306 and 2.14±0.162 hour, respectively, for AD and ND patients) (33). Two AD-affected brain regions were analysed, inferior temporal lobe grey matter and hippocampus. Protein extracts were prepared by sonication with 5 volumes of extracting buffer (2% SDS, 1 mM EDTA, and protease inhibitors in PBS) and 8 μg of protein from each brain extract were loaded onto reducing NuPAGE 4-12% Bis-Tris gel (Invitrogen, Carlsbad, Calif.). Immunoblotting was performed with specific antibodies to ABAD (monoclonal antibody to human, generated in our lab, 1:10,000) or (3-actin (1:10,000, Sigma, St. Louis, Mo.). The immunoreactive bands were detected with Super Signal Pico Chemiluminescent substrate (Pierce Chemicals). Densitometry was performed using the Chemilmager 4000 Imaging system (Alpha Innotech, San Leandro, Calif.) to determine differences in intensity of the ABAD immunoreactive band, which was normalized according to intensity of the (3-actin band. Our results demonstrate a significant increase of ABAD protein in the AD-pathology-affected regions (approximately 28% increase in inferior temporal lobe grey matter and 40% in hippocampus) from AD patients versus ND controls. These data are consistent with our previous data (1) demonstrating enhanced expression of ABAD in AD brain by immunoblotting with anti-ABAD antibody. In contrast, protein extracts prepared from the cerebellum, a region spared from the AD pathology, showed no significant differences between AD patient and ND controls.

If the above results in cell culture could be extrapolated to in vivo settings, then mice overexpressing ABAD in an Aβ-rich environment, i.e., Tg mAPP/ABAD mice, might exhibit exaggerated oxidative stress and elevated generation of ROS. Electron paramagnetic spin resonance (EPR) spectroscopy was used to measure the level of ROS in intact frozen brain at 77° K (FIG. 4A). Dramatically higher amounts of radicals, as shown by the sharp peak at 3410 Gauss, were observed in the Tg mAPP/ABAD mouse brains, in comparison with brains from nonTg, Tg ABAD or Tg mAPP mice. It is evident that this species of free radicals, which might be from ascorbyl or the one-electron reduced ubiquinone radical, is generated as a result of higher levels of oxidative stress in Tg mAPP/ABAD (12), compared to the other genotypes.

Excessive generation of ROS could result in neuronal dysfunction, or, alternatively, could be buffered by protective anti-oxidant mechanisms without changes in neuronal function. The radial-arm water maze test was used to detect hippocampal-dependent learning/memory deficits in Tg mAPP/ABAD mice (13, 14). Young mice (4.5-5 months of age) of nonTg, Tg mAPP or Tg ABAD transgenic littermates, all showed strong learning and memory capacity. As they sought out the new platform location, they averaged less than 1-2 errors by trials 4 or 5 (FIG. 4B). In contrast, Tg mAPP/ABAD mice failed to learn efficiently and still averaged about 4 errors by trials 4 or 5 (FIG. 4B), indicative of severe impairment in spatial and temporal memory.

Double transgenic expression of ABAD and mAPP did not cause impairment in vision, motor coordination or motivation. The visible platform test showed that the four genotypes exhibited no difference in their speed of swimming and in their latencies to find the platform (FIG. 4C).

The data demonstrate that ABAD and Aβ directly interact in mitochondria in AD, and that this interaction promotes leakage of ROS, mitochondrial dysfunction and cell death, potentially underlying the mechanism of Aβ-induced mitochondrial toxicity (15-22). Such events are likely to induce changes in behavior, characterized by exaggerated impairment of hippocampal function in Tg mAPP/ABAD mice. Taken together, these studies establish that Aβ may exert an important pathogenic role in the mitochondrial compartment through an interaction with ABAD and that inhibition of ABAD-Aβ interaction may provide a new treatment strategy against AD.

TABLE 1

Mutational studies of ABAD.

| ABAD mutations | Aβ Binding* |
|---|---|
| Experiments with ABAD truncations† | |
| GST-ABAD(1-186) | + |
| GST-ABAD(1-158) | + |
| GST-ABAD(159-261) | − |
| Experiments with site-directed ABAD mutations† | |
| G93A | + |
| S98A, K99A | + |
| S98A, K99A, T100A, Y101A | − |
| S98A, K99A, Y101A | − |
| N102A | + |
| N102A, L103A | + |
| T108A, H109A, T110A | − |
| V156A | + |
| Q162A | + |

*+: Specific binding comparable to that observed with wild type ABAD; −: No observed specific binding.
†Binding of $^{125}$I-labeled GST-ABAD or ABAD to immobilized Aβ (1-42) as previously described (I).

TABLE 2

Crystallographic statistics.

| Crystals of the ABAD/Aβ complex | |
|---|---|
| Space group | P432 |
| Cell dimensions | a = 130.0 Å |
| Diffraction Data | |
| Resolution | 30-2.3 Å |
| $R_{sym}$ (last shell) | 5.1% (15.2%) |
| Completeness (last shell) | 99.8% (99.8%) |
| I/SigI (last shell) | 57.7 (13.0) |
| Molecular Replacement | |
| Resolution | 10-4.0 Å |
| Number of rotations searched | 181 |
| Correlation coefficient | 32.4% |
| R | 44.3% |
| Refinement | |
| Resolution | 30-2.3 Å |
| Sigma cutoff | 0.0 |
| Number of protein residues | 208 |
| Number of protein atoms | 1480 |
| Number of solvent and ion atoms | 121 |
| Number of reflections used | 17049 |
| R ($R_{free}$) | 23.1% (26.1%) |
| RMSD bond length | 0.006 Å |
| RMSD bond angle | 1.1° |

TABLE 3

ABAD interaction.

| Peptide | $K_d$(nM) |
|---|---|
| Aβ 1-40 | 38.4 ± 4.6 |
| Aβ 1-42 | 55.8 ± 10.9 |
| Aβ 1-20 | 88.9 ± 19.9 |
| Aβ 25-35 | >$10^3$ |
| PrP 109-141 | >$10^6$ |
| Amylin | >$10^7$ |

*These studies were performed by immobilizing the indicated amyloid-related peptide on microtiter wells followed by blocking excess sites in the well, and then doing a binding assay by addition of fluorescein-labeled ABAD. Similar results were obtained using a radioligand binding assay ($^{125}$I-labeled ABAD).

REFERENCES

1. S. D. Yan, at al., *Nature* 389, 689-95 (1997).
2. K. Beyreuther, C. L. Masters, *Nature* 389, 677-8 (1997).
3. S. D. Yan, et al., *J Biol Chem* 274, 2145-56 (1999).
4. U. C. Oppermann, S. Salim, L. O. Tjernberg, L. Terenius, H. Jornvall, *FBS Lett* 451, 238-42 (1999).
5. L. Torroja, D. Ortuno-Sahagun, A. Ferrus, B. Hammerle, J. A. Barbas, *J Cell Biol* 141, 1009-17 (1998).
6. L. Mucke, et al., *J Neurosci* 20, 4050-8 (Jun. 1, 2000).
7. S. D. Yan, at al., *J Biol Chem* 275, 27100-9 (2000).
8. A. J. Powell, et al., *J Mol Biol* 303, 311-27 (2000).
9. M. A. Abreo, et al., in *US Patent and Trademark Office* (USA, 2002), vol. 9.
10. M. Aarts, at al., *Science* 298, 846-50 (Oct. 25, 2002).
11. M. Becker-Hapak, S. S. McAllister, S. F. Dowdy, *Methods* 24, 247-56 (July, 2001).
12. H. P. Grill, J. L. Zweier, P. Kuppusamy, M. L. Weisfeldt, J. T. Flaherty, *J Am Coll Cardiol* 20, 1604-11 (December 1992).
13. D. Morgan, at al., *Nature* 408, 982-5 (Dec. 21-28, 2000).
14. G. Di Rosa, T. Odrijin, R. A. Nixon, O. Arancio, *J Mol Neurosci* 19, 135-41 (August-October 2002).
15. R. H. Swerdlow, S. J. Kish, *Int Rev Neurobiol* 53, 341-85 (2002).
16. R. Castellani, et al., *J Neurosci Res* 70, 357-60 (Nov. 1, 2002).
17. A. D. Cash, et al., *Neuroscientist* 8, 489-96 (October 2002).
18. J. P. Blass, *Int Rev Neurobiol* 51, 325-76 (2002).
19. A. C. Rego, C. R. Oliveira, *Neurochem Res* 28, 1563-74 (October 2003).
20. G. Aliev, et al., *Neurol Res* 25, 665-74 (September 2003).
21. J. P. Blass, *Neural Res* 25, 556-66 (September 2003).
22. M. P. Mattson, *Int Rev Neurobiol* 53, 387-409 (2002).
23. H. K. Anandatheerthavarada, G. Biswas, M. A. Robin, N. G. Avadhani, *J Cell Biol* 161, 41-54 (Apr. 14, 2003).
24. Z. Otwinowski, W. Minor, *Methods Enzymol.* 276, 307-326 (1997).
25. L. Tong, *J. Appl. Cryst.* 26, 748-751 (1993).
26. A. T. Brunger et al., *Acta Crystallogr. D* 54, 905-21 (1998).
27. T. A. Jones, J.-Y. Zou, S. W. Cowan, M. Kjeldgaard, *Acta Crystallgr. A* 47, 110-119 (1991).
28. S. V. Evans, *J. Mol. Graph.* 11, 134-8 (1993).
29. T. Valdes-Gonzalez, J. Inagawa, T. Ido, *Peptides* 22, 1099-106 (July, 2001).
30. K. Takuma, et al., *J Biol Chem* 276, 48093-9 (Dec. 21, 2001).
31. J. P. Crow, *Nitric Oxide: Biology and Chemistry* 1, 145-157 (1997).
32. N. W. Kooy, J. A. Royall, H. Ischiropoulos, *Free Radio Res* 27, 245-54 (September 1997).
33. L. F. Lue et al., *Experimental Neurology* 171, 29-45 (2001).

What is claimed is:

1. An isolated polypeptide consisting of a portion of Aβ-binding alcohol dehydrogenase (ABAD), wherein the portion of ABAD binds to Aβ protein and consists of the sequence of amino acid residues 94-114 of human ABAD, the sequence of which residues is set forth in SEQ ID NO:4.

2. A composition of matter comprising (a) a pharmaceutical carrier and (b) the isolated polypeptide of claim 1.

3. The composition of matter of claim 2, wherein the composition binds to Aβ protein.

4. A composition of matter comprising a protein of SEQ ID NO:1 or 2 (Tat protein) operatively affixed to a portion of a human ABAD protein, wherein the portion of the human ABAD protein consists of amino acid residues 94-114 of the human ABAD protein, the sequence of which residues is set forth in SEQ ID NO:4.

* * * * *

SEQUENCE LISTING

<160> NUMBER OF SEQ ID NOS: 14

<210> SEQ ID NO 1
<211> LENGTH: 86
<212> TYPE: PRT
<213> ORGANISM: Human immunodeficiency virus

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
            85

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg
1               5                   10

<210> SEQ ID NO 3
<211> LENGTH: 29
<212> TYPE: PRT
<213> ORGANISM: Human

<400> SEQUENCE: 3

Ala Gly Ile Ala Val Ala Ser Lys Thr Tyr Asn Leu Lys Lys Gly Gln
1               5                   10                  15

Thr His Thr Leu Glu Asp Phe Gln Arg Val Leu Asp Val
            20                  25

<210> SEQ ID NO 4
<211> LENGTH: 21
<212> TYPE: PRT
<213> ORGANISM: Human

<400> SEQUENCE: 4

Ile Ala Val Ala Ser Lys Thr Tyr Asn Leu Lys Lys Gly Gln Thr His
1               5                   10                  15

Thr Leu Glu Asp Phe
            20

<210> SEQ ID NO 5
<211> LENGTH: 20
<212> TYPE: PRT
<213> ORGANISM: Human

<400> SEQUENCE: 5

Asp Ala Glu Phe Arg His Asp Ser Gly Tyr Glu Val His His Gln Lys
1               5                   10                  15

Leu Val Phe Phe
            20

<210> SEQ ID NO 6
<211> LENGTH: 19
<212> TYPE: PRT
<213> ORGANISM: Human

<400> SEQUENCE: 6

Ala Val Ala Ser Lys Thr Tyr Asn Leu Lys Lys Gly Gln Thr His Thr
1               5                   10                  15

Leu Glu Asp

<210> SEQ ID NO 7
<211> LENGTH: 19
<212> TYPE: PRT
<213> ORGANISM: Rat

<400> SEQUENCE: 7

Ala Val Ala Ile Lys Thr Tyr His Glu Lys Lys Asn Gln Val His Thr
1               5                   10                  15

Leu Glu Asp

<210> SEQ ID NO 8
<211> LENGTH: 19
<212> TYPE: PRT
<213> ORGANISM: Mouse

<400> SEQUENCE: 8

Ala Val Ala Ile Lys Thr Tyr His Gln Lys Lys Asn Lys Ile His Thr
1               5                   10                  15

Leu Glu Asp

<210> SEQ ID NO 9
<211> LENGTH: 19
<212> TYPE: PRT
<213> ORGANISM: Bovine

<400> SEQUENCE: 9

Ala Val Ala Ser Lys Thr Tyr Asn Leu Lys Lys Ser Gln Ala His Thr
1               5                   10                  15

Leu Glu Asp

<210> SEQ ID NO 10
<211> LENGTH: 19
<212> TYPE: PRT
<213> ORGANISM: Drosophila

<400> SEQUENCE: 10

Ala Thr Ala Val Lys Thr Phe Asn Phe Asn Lys Asn Val Ala His Arg
1               5                   10                  15

Leu Glu Asp

<210> SEQ ID NO 11
<211> LENGTH: 6
<212> TYPE: PRT
<213> ORGANISM: Human

<400> SEQUENCE: 11

Gly Pro Gln Thr Lys Val
1               5

```
<210> SEQ ID NO 12
<211> LENGTH: 12
<212> TYPE: PRT
<213> ORGANISM: Human

<400> SEQUENCE: 12

Gly Gly Pro Lys Pro Phe Asp Met Pro Met Ala Asp
1               5                   10

<210> SEQ ID NO 13
<211> LENGTH: 13
<212> TYPE: PRT
<213> ORGANISM: Human

<400> SEQUENCE: 13

Gly Leu Leu Gly Pro Leu Glu Ala Leu Gly Glu Asp Ala
1               5                   10

<210> SEQ ID NO 14
<211> LENGTH: 13
<212> TYPE: PRT
<213> ORGANISM: Streptomyces exfoliatus

<400> SEQUENCE: 14

Ser Thr Gly Met Phe Leu Glu Thr Glu Ser Val Glu Arg
1               5                   10
```